US005713932A

United States Patent [19]
Gillberg et al.

[11] Patent Number: 5,713,932
[45] Date of Patent: Feb. 3, 1998

[54] METHOD AND APPARATUS FOR DETERMINING ATRIAL LEAD DISCLOCATION AND CONFIRMING DIAGNOSIS OF ATRIAL TACHYARRHYTHIMIAS

[75] Inventors: Jeffrey M. Gillberg, Coon Rapids; Mark L. Brown, North Oaks, both of Minn.

[73] Assignee: Medtronic, Inc., Minneapolis, Minn.

[21] Appl. No.: 738,769

[22] Filed: Oct. 28, 1996

[51] Int. Cl.$^6$ ........................................ A61N 1/37
[52] U.S. Cl. ................................... 607/27; 607/9
[58] Field of Search ........................ 607/4, 5, 9, 25, 607/27, 28, 63

[56] References Cited

U.S. PATENT DOCUMENTS

| | | |
|---|---|---|
| 4,248,238 | 2/1981 | Joseph . |
| 4,316,472 | 2/1982 | Mirowski et al. . |
| 4,577,633 | 3/1986 | Berkovits . |
| 4,860,749 | 8/1989 | Lehmann . |
| 4,953,551 | 9/1990 | Mehra et al. . |
| 5,117,824 | 6/1992 | Keimel et al. . |
| 5,163,427 | 11/1992 | Keimel . |
| 5,188,105 | 2/1993 | Keimel et al. . |
| 5,201,865 | 4/1993 | Kuehn . |
| 5,330,508 | 7/1994 | Gunderson . |
| 5,342,402 | 8/1994 | Olson . |
| 5,383,910 | 1/1995 | den Dulk ................................ 607/14 |
| 5,558,098 | 9/1996 | Fain ....................................... 607/5 |

FOREIGN PATENT DOCUMENTS

| | | |
|---|---|---|
| WO 92/18198 | 10/1992 | WIPO . |
| WO 95/28987 | 11/1995 | WIPO . |
| WO 95/28988 | 11/1995 | WIPO . |

OTHER PUBLICATIONS

Leong et al., "Matic An Intracardiac Classification System-"*PACE*, vol. 15, Sep. 1992, pp. 1217–31.
R, Arzbaecher et al., "Automatic Tachycardia Recognition", *PACE*, vol. 7, pp. 541–547, May–Jun. 1984, Part II.
den Dulk et al., "Is There a Universal Antitachycardia Pacing Mode", *Am. J. Cardiology*, 1986, 57:950–5.
S. Furman et al., "Necessity of Signal Processing in Tachycardia Detection", *The Third Decade of Cardiac Pacing: Advances in Technology in Clinical Applications*, Futura Publishing, 1982, pp. 265–274.

*Primary Examiner*—William E. Kamm
*Assistant Examiner*—George R. Evanisko
*Attorney, Agent, or Firm*—Reed A. Duthler; Harold R. Patton

[57] ABSTRACT

In a dual chamber cardiac stimulators, e.g. cardiac pacemaker or pacemaker/cardioverter/defibrillator (PCD) system, which relies upon the detection of atrial depolarizations or the stimulation of the atria in the performance of a defined function, a method and apparatus for determining the existence of an atrial pace/sense electrode(s) dislocation from an atrial site to a position inferior to the AV node of the heart thereby affecting a function, e.g. providing a false indication of atrial tachyarrhythmia. The determination of the occurrence of a dislocation of the atrial pace/sense electrode is effected by applying a test pace pulse to the atrial pace/sense electrode; detecting the immediately following ventricular depolarization from a ventricular sense electrode; measuring the interval between the delivered atrial pace pulse and the detected ventricular depolarization; comparing the measured interval to a threshold AV interval; and determining that the atrial pace/sense electrode is in contact with the right atrium if the measured interval is longer than the threshold AV interval. Preferably, the determination is effected by: providing a first signal when the measured AV interval exceeds the threshold AV interval and a second signal when the measured AV interval is less than the threshold AV interval; applying a series of M atrial pace pulses to the atrial pace/sense electrode; counting the number of first and second signals provided in response to the series of atrial pace pulses; and determining that the atrial pace/sense electrode is located in the right atrium when a number of first signals are provided in a series of delivered atrial pace pulses. Confirmation of a provisional tachyarrhythmia is also made from the number of first and second signals.

30 Claims, 7 Drawing Sheets

METHOD AND APPARATUS FOR DETERMINING ATRIAL LEAD DISCLOCATION AND CONFIRMING DIAGNOSIS OF ATRIAL TACHYARRHYTHMIAS

CROSS-REFERENCE TO RELATED APPLICATIONS

Reference is hereby made to commonly assigned co-pending U.S. patent application Ser. No. 08/649,145 filed May 14, 1996 for PRIORITIZED RULE BASED METHOD AND APPARATUS FOR DIAGNOSIS AND TREATMENT OF ARRHYTHMIAS in the name of Gillberg et al.

FIELD OF THE INVENTION

This invention relates to dual chamber cardiac stimulators, e.g. cardiac pacemaker or pacemaker/cardioverter/defibrillator (PCD) systems which rely upon the detection of atrial depolarizations in the performance of a defined function, and to a method and apparatus for determining the existence of an atrial pace/sense electrode(s) dislocation from an atrial site to a position inferior to the AV node of the heart thereby affecting a function, e.g. providing a false indication of atrial tachyarrhythmia.

BACKGROUND OF THE INVENTION

Current dual chamber, multi-mode, cardiac pacemakers typically employ atrial and ventricular endocardial pacing leads having one or two distally located pace/sense electrodes that are adapted to be attached in the right atrium and right ventricle, respectively, and operate to sense the atrial and ventricular electrogram (EGM) and deliver pacing pulses to each chamber, depending on the operating mode. Dual chamber demand cardiac pacing is dependent upon the retention of the atrial pace/sense electrode(s) at the atrial site. The dislocation of the atrial pace/sense electrode(s) to a location inferior to the AV node can result in the loss of sensing of the atrial EGM events (principally the P-wave). However, the R-wave of the ventricular EGM as well as other electrical signal peaks of the QRST complex may be readily detected if there is good electrode-tissue contact or may be intermittently detected if the electrode-tissue contact is intermittent. The relatively high gain setting of the atrial sense amplifier necessary to sense the relatively low amplitude P-wave may also contribute to mistaken "sensing" of peaks of the QRST complex and other spurious signals as P-waves. As a result, the atrial and ventricular pacing may be inhibited (which may not be undesirable under the circumstances) or become erratic, which could cause a ventricular pacing pulse to be delivered at an undesirable time in the pacing cycle, possibly provoking a tachyarrhythmia. At the least, the benefits of synchronous dual chamber pacing in sustaining a physiologic heart rate and adequate cardiac output would be lost.

In proposed dual chamber PCD systems having the capability of detecting and treating atrial arrhythmias with at least a limited menu of anti-tachyarrhythmia therapies, also referred to as supraventricular arrhythmias and including atrial fibrillation and atrial flutter, the correct diagnosis of the nature of a detected tachyarrhythmia so that an appropriate treatment can be delivered is crucial. Typically, in proposed dual chamber PCD systems, at least both atrial and ventricular pacing and sensing functions are provided in conjunction with tachyarrhythmia detection and anti-tachyarrhythmia therapy delivery in at least one of the chambers. Such dual chamber PCD systems may only provide atrial anti-tachycardia pacing therapies of the types described below or may include atrial cardioversion/defibrillation capabilities as further described below. The failure to deliver the appropriate therapy or the delivery of an inappropriate therapy to treat an apparent atrial tachyarrhythmia can progress to or trigger more serious ventricular tachyarrhythmia. Consequently, a great deal of effort has been undertaken to refine the diagnosis of the tachyarrhythmia and to define the appropriate therapy in response to the diagnosis.

The article "Automatic Tachycardia Recognition" by R. Arzbaecher et al., PACE, May–June 1984, pp. 541–547 discloses an algorithm intended to be implemented in a microprocessor based implantable device employing both atrial and ventricular rate detection via separate bipolar leads in order to measure the intrinsic or evoked A-A and V-A, or V-V escape intervals and AV delay intervals in order to distinguish among various types of atrial and ventricular tachycardias, fibrillation or flutter. The Arzbaecher et al. article also discloses the concept of employing a premature atrial pace stimulus that is delivered to the atrial pace/sense electrode to distinguish 1:1 sinus tachycardia from 1:1 paroxysmal tachycardia. When a 1:1 sinus or paroxysmal tachycardia is determined from a series of A-A and V-V intervals, the atrial pace pulse is applied at a time in the VA interval when it would be expected to elicit a ventricular response, i.e., an R-wave, after an AV propagation delay interval. If the tachycardia is sinus in origin, the R-wave will consistently follow the premature atrial pace pulse within a consistent AV delay. If there is no conducted ventricular response, the following R-wave will appear at the end of the prevailing V-V interval, signifying that the tachycardia is AV re-entrant or ventricular in origin with VA conduction because the atrial premature depolarization reaches the AV node when it is refractory.

Other proposals for employing atrial and ventricular detection and interval comparison are set forth in *The Third Decade Of Cardiac Pacing: Advances in Technology in Clinical Applications*, Part III, Chapter 1, "Necessity of Signal Processing in Tachycardia Detection" by Furman et al. (edited by S. Barold and J. Mugica, Futura Publications, 1982, pages 265–274) and in U.S. Pat. No. 4,860,749 to Lehmann. In both cases, atrial and ventricular rates or intervals are compared to one another in order to distinguish sinus and pathological tachycardias.

A recent article, "MATIC—An Intracardiac Tachycardia Classification System", by Leong et al., PACE, Vol. 15, September 1992, Pages 1317–1331, discloses an automated tachycardia analysis system which employs a neural network for morphology analysis and which compares measured A-V intervals to measured V-V intervals for classification of tachycardias displaying 1:1 correspondence between atrial and ventricular depolarizations.

In commonly assigned, U.S. Pat. No. 5,383,910 issued to den Dulk, incorporated herein by reference, a method is described for distinguishing AV nodal reentrant tachycardias from other tachycardias which exhibit 1:1 correspondence between atrial and ventricular rhythms. Atrial and ventricular cycle lengths (ACL's and VCL'S, respectively) are determined from the respective atrial and ventricular electrocardiograms and for determining whether the VCLs (and optionally the ACLs) reflect a ventricular and/or atrial rate exceeding a preset tachycardia rate threshold.

If the ventricular rate (or optionally the atrial rate) indicates the presence of a tachycardia, the method determines whether closely spaced atrial and ventricular depolarizations, in either order, occur sequentially within a series of heart cycles. Such closely spaced atrial and ventricular depolarizations are considered to be indicative of reentrant AV nodal tachycardia if they are within a short, defined time interval less than would be expected in a sinus tachycardia which occurs at a rate which meets the criteria for tachycardia detection. This defined time interval may be, for example, up to 50–100 ms, with intervals of 80 msec or less preferred. A series of a predetermined number of successive closely spaced atrial and ventricular depolarizations satisfying this criteria results in a diagnosis of AV nodal reentrant tachycardia and the delivery of a therapy particularly adapted to terminate such an arrhythmia, e.g. the therapies described in the above-incorporated '910 patent.

In some of these proposed dual chamber PCD systems (and in existing single chamber PCD systems), one or two basic strategies are generally followed. A first strategy is to identify heart events, event intervals or event rates as they occur as indicative of the likelihood of the occurrence of specific types of arrhythmias, with each arrhythmia having a preset group of criteria which must be met as precedent to detection or classification. As events progress, the criteria for identifying the various arrhythmias are all monitored simultaneously, with the first set of criteria to be met resulting in detection and diagnosis of the arrhythmia. A second strategy is to define a set of criteria for events, event intervals and event rates which is generally indicative of a group of arrhythmias, and following those criteria being met, analyzing preceding or subsequent events to determine which specific arrhythmia is present. In the Medtronic Model 7219 devices, an arrhythmia detection and classification system generally as disclosed in U.S. Pat. No. 5,342,402, issued to Olson et al., incorporated herein by reference in its entirety, is employed, which uses both strategies together.

In the above-referenced Gilberg et al application, an arrhythmia detection and classification system is described wherein a prioritized set of inter-related rules for arrhythmia detection and discrimination are employed. Each rule contains a set of one or more "clauses" which must be satisfied (criteria which must be met). While all clauses of a rule are satisfied, the rule is indicated to be met (referred to as the rule "firing"). It is possible for multiple rules to be "firing" at the same time, with the highest priority rule taking precedence. Some rules trigger delivery of therapy when firing, whereas other rules inhibit delivery of therapy when firing. The highest priority rule firing at any specific time controls the behavior of the device. For example, the firing of a rule which triggers therapy is superseded by the firing of higher priority rules preventing delivery of therapy. Rules cease firing when their clauses cease to be satisfied, whether or not a therapy is triggered by the rule.

Each rule includes a set of clauses or criteria which, when satisfied, indicate the likely occurrence of a specified type of heart rhythm, including various tachyarrhythmias, sinus tachycardia and normal sinus rhythm. A specific rhythm or tachyarrhythmia may have more than one associated rule. The rules are interrelated, such that progress toward meeting the requirements of a clause of one role may also be the subject matter of a clause of a different role.

The specific criteria set forth by the clauses of the various rules as disclosed include a number of known criteria for evaluating heart rhythm, including the entire arrhythmia detection and classification system employed in the presently available Medtronic 7219 pacemaker cardioverter defibrillators, as well as criteria disclosed in U.S. Pat. No. 5,330,508, issued to Gunderson. In addition, a number of new evaluation criteria are included within the clauses of various rules disclosed in the Gilberg et al application. One such new detection methodology is based upon the classification of the events occurring associated with the sequence of two ventricular depolarizations into a limited number of event patterns, based upon the number and times of occurrences of atrial events, preceding the two most recent ventricular events. An event pattern is developed for each individual ventricular event, so that successive event patterns overlap one another. Certain sequences of event patterns are strongly indicative of specific types of heart rhythms. For heart rhythms of which this is true, a defined set of indicative event pattern sequences or a "grammar" is defined. Adherence of the heart rhythm to the grammars associated with various heart rhythms is determined by simultaneously operating continuous recognition machines, the outputs of which form the subject matter of one or more clauses, within the hierarchy of rules.

In a preferred embodiment of the invention disclosed in the Gilberg et al application, the device is provided with rules which when satisfied indicate the presence of sustained atrial fibrillation and sustained atrial flutter and in response to detection thereof delivers anti-atrial fibrillation or anti-atrial tachycardia therapies. These rules include a set of various new classification criteria, including an atrial fibrillation/atrial tachycardia evidence counter which is incremented and decremented on a beat by beat basis and compared with a defined threshold count or counts taken as indicative of atrial fibrillation or atrial tachycardia. The atrial rate and regularity is also monitored and atrial fibrillation or atrial tachycardia is preliminarily detected when the evidence counter is at or above such a threshold and the atrial rhythm meets defined rate zone criteria associated with atrial fibrillation or atrial tachycardia. When both the evidence count and the rate zone criteria are met, the arrhythmia underway is preliminarily determined to be atrial fibrillation or atrial tachycardia, depending on which rate zone criteria are met. A sustained atrial fibrillation/atrial tachycardia duration timer is then initiated and continues to time until termination of atrial tachyarrhythmia is detected. The time duration since the provisional detection of an atrial tachyarrhythmia is continually compared to one or more minimum duration values associated with the atrial tachyarrhythmia determined to presently be underway and/or the next scheduled therapy for such arrhythmia. If the time duration since provisional detection of atrial arrhythmia meets or exceeds the applicable minimum duration value, and other associated criteria are also met, the next scheduled anti-atrial arrhythmia therapy is delivered.

Additional associated criteria which must be met as a prerequisite to delivery of atrial anti-tachyarrhythmia therapies may include expiration of a minimum interval from the most recently delivered therapy not followed by a detected termination of atrial tachyarrhythmia, confirmation that the most recent heart cycles do not indicate a return to sinus rhythm, time duration since provisional detection of atrial tachyarrhythmia being less than a maximum duration value, time of day corresponding to a pre-defined time range and/or less than a preset number of atrial anti-arrhythmia therapies having been delivered in a preceding time period.

In such complex arrhythmia determination and discrimination systems as described above, it is assumed that the atrial pace/sense electrodes are fixed in the right atrial heart chamber superior to the AV node. For example, such a presumption prevails in the method of distinguishing 1:1 sinus tachycardia from 1:1 paroxysmal tachycardia proposed by Arzbaecher et al. as described above. In the vast majority of implantations, unipolar or bipolar atrial pace/sense electrodes are introduced into the right atrium and typically lodged in the right atrial appendage or wall where they remain in place. Fixation of the electrode(s) is effected either with a passive fixation mechanism, e.g. soft pliant tines that engage in the trabecular structure of the right atrial appendage, or an active fixation mechanism, e.g. a helical coil distal tip electrode that is screwed into a relatively thick portion of the right atrial wall. Despite the efforts to maintain fixation, the atrial pace/sense electrode(s) can, on rare occasion, become dislodged and migrate through the tricuspid valve into the right ventricle at some time after implantation and medical discharge of the patient.

In such a dislocation position, the electrogram signals that are processed as atrial sense events may actually reflect the activity of the atria and the ventricles or just the ventricles or reflect oversensing due to intermittent contact of the electrode(s) with the endocardium and the gain setting of the atrial sense amplifier. The resulting sequences of event patterns derived from the ventricular and atrial sense amplifiers can be erroneously interpreted by the algorithm as representing an atrial tachyarrhythmia, and the device can trigger delivery of a programmed therapy for that tachyarrhythmia.

In this regard, the dual chamber PCD systems under development and described in the above-referenced patents typically provide a programmable menu of therapies including a variety of atrial anti-tachycardia pacing and cardioversion/defibrillation shock therapies. The delivery of a cardioversion/defibrillation therapy may be confined to atrial cardioversion/defibrillation electrodes and timed to a ventricular sense event to help ensure against provoking a ventricular arrhythmia, particularly ventricular fibrillation. Atrial anti-tachycardia single pulse and pulse train therapies are also typically delivered in timed relation to the atrial sense events to avoid accelerating the atrial rate or arrhythmia or triggering a ventricular arrhythmia. If the atrial sense amplifier is not sensing atrial events because of the dislocation of the atrial pace/sense electrode(s), the delivery of these atrial tachyarrhythmia therapies may provoke a life threatening ventricular fibrillation episode. Although a dual chamber PCD system with ventricular anti-tachyarrhythmia therapy capabilities may be prepared to respond to the device triggered ventricular fibrillation, the episode and shock delivered to the patient is upsetting at the least. And recourse to such a fail-safe ventricular shock therapy is absent from PCD systems or anti-tachyarrhythmia pacing therapy devices only having atrial anti-tachyarrhythmia therapy capabilities.

Moreover, in such dual chamber PCD systems, the misdiagnosis of an atrial tachyarrhythmia due to the dislocation of the atrial pace/sense electrode(s) may mask a more serious ventricular tachyarrhythmia and either prevent or delay delivery of an appropriate ventricular cardioversion/defibrillation therapy.

SUMMARY OF THE INVENTION

Consequently, it is a primary object of the present invention to determine, in implantable systems of the types described above that the atrial pace/sense electrode(s) are properly located in the right atrium and not dislocated into a location inferior to the AV node and/or in the right ventricle.

It is a further object of the present invention to determine, in dual chamber or atrial chamber only PCD systems that the provisional determination of an atrial tachyarrhythmia is correct and not resulting from displacement of the atrial pace/sense electrode(s) into a location inferior to the AV node and/or into the right ventricle.

In accordance with the present invention, the determination of the occurrence of a dislocation of the atrial pace/sense electrode(s) in a system of the types described above is effected through the means of and steps for: applying a pace pulse to an atrial pace electrode(s); detecting the immediately following ventricular depolarization from a ventricular sense electrode(s); measuring the interval between the delivered atrial pace pulse and the detected ventricular depolarization; comparing the measured interval to a threshold AV interval; and determining that the atrial pace electrode(s) is in contact with the right atrium if the measured interval is longer than the threshold AV interval.

Preferably, the determination further comprises the means for and steps of: providing a first signal when the measured AV interval exceeds the threshold AV interval and a second signal when the measured AV interval is less than the threshold AV interval; applying a series of atrial pace pulses to the atrial pace electrode(s); counting the number of first and second signals provided in response to the series of atrial pace pulses; and determining that the atrial sense electrode(s) of the atrial lead are located in the right atrium when a series of first signals are consistently provided as a result of the series of atrial pace pulses.

In addition, the inventive method and apparatus further comprises the steps of and means for determining that the atrial sense electrode(s) of the atrial lead are located in the right ventricle when a series of second signals are consistently provided as a result of the series of atrial pace pulses.

The threshold AV interval is selected to be a fraction of a normal AV conduction time for the prevailing sensed V-V interval. The series of atrial pace pulses are delivered after a VA interval that is also a fraction of the prevailing sensed V-V interval calculated to avoid delivering the atrial pace pulse in the T-wave of a preceding ventricular depolarization to avoid provoking a ventricular tachyarrhythmia if the atrial pace/sense electrode(s) is in the right ventricle.

The atrial lead test apparatus and method of the present invention may be automatically caused to operate in response to a triggering event, e.g. at a particular time of day or number of system operations or may be triggered to operate by an action, e.g. a programmed in command from an external programmer.

In a further preferred embodiment of the present invention with particular application to dual chamber PCD systems, the atrial lead test apparatus and method of the present invention may be triggered to operate in response to a provisional determination of an atrial tachyarrhythmia. Moreover, in this context, the appropriateness of the provisional determination may be tested by the apparatus and method of the present invention whereby the provisonally determined atrial tachyarrhythmia is confirmed as a result of the determination of the location of the atrial pace/sense electrode(s) in the right atrium or not confirmed as a result of the determination of the location of the atrial pace/sense electrode(s) outside the right atrium.

More specifically, the provisionally diagnosed atrial tachyarrhythmia is confirmed and the selected therapy delivered when the first signal is provided from the comparison (i.e., when the sensed AV interval exceeds the threshold AV interval), and preferably when a series of the first signals are provided. Conversely, the provisionally diagnosed atrial tachyarrhythmia is not confirmed and the selected therapy is not delivered when the second signal is provided from the comparison (i.e., when the sensed AV interval is less than the threshold AV interval), and preferably when a series of second signals are provided. Moreover, when a series of both first and second signals are provided in a single test, this factor is used to confirm or bias the determination that the atrial tachyarrhythmia is atrial fibrillation or flutter.

The method and apparatus of the present invention provides a simple mechanism to confirm the location of the atrial pace/sense electrode(s) in systems of the type described above. In dual chamber PCD systems of the type described above, potential injury to the patient is avoided when an atrial anti-tachyarrhythmia therapy is not delivered that would provoke a more serious ventricular tachyarrhythmia or a ventricular anti-tachyarrhythmia therapy is delivered when it is required.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
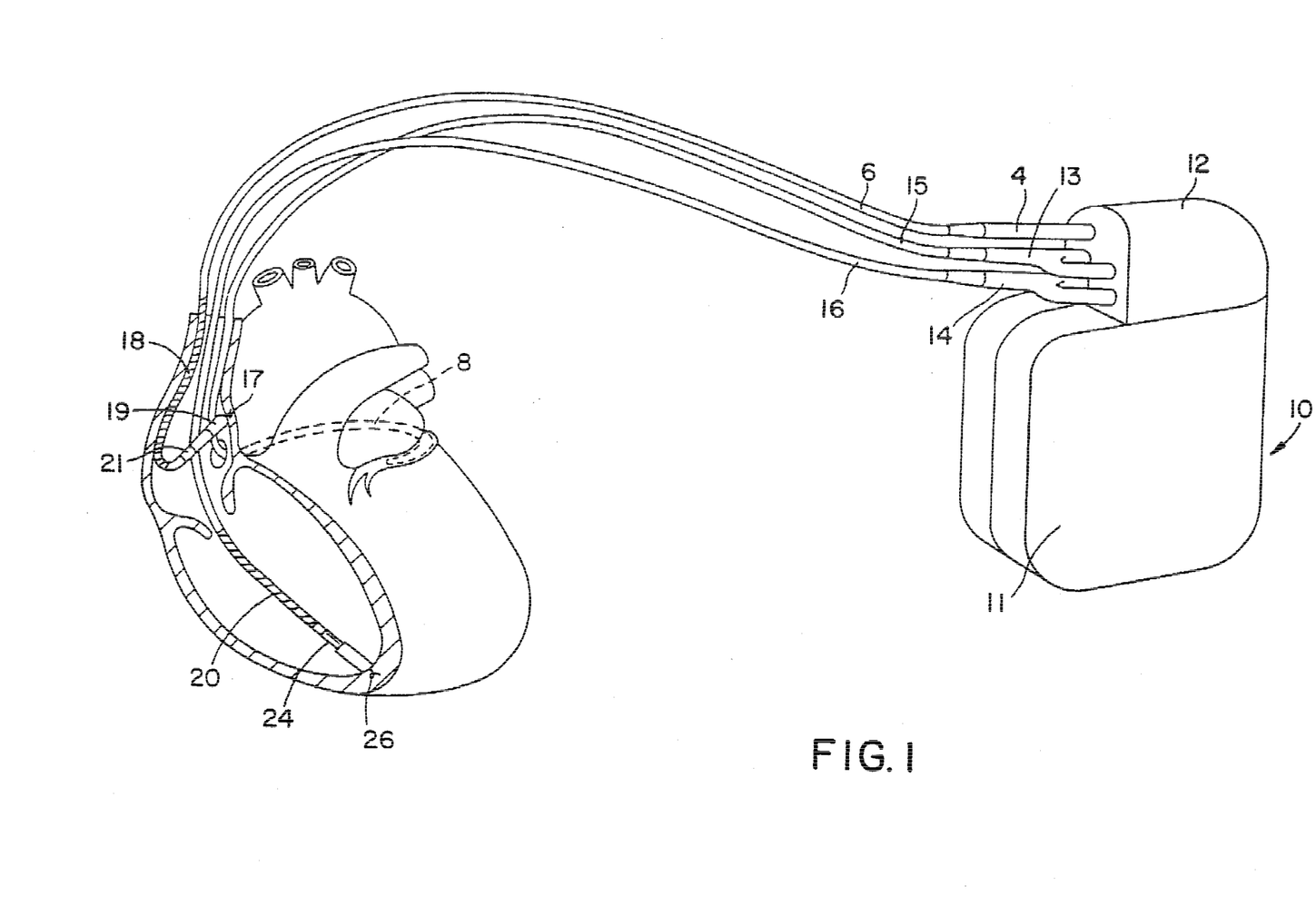
FIG. 1 illustrates a first embodiment of an implantable PCD system of a type appropriate for use in practicing the present invention, in conjunction with a human heart wherein the atrial pace/sense electrodes of an atrial lead are properly located in the right atrium.
Figure 2:
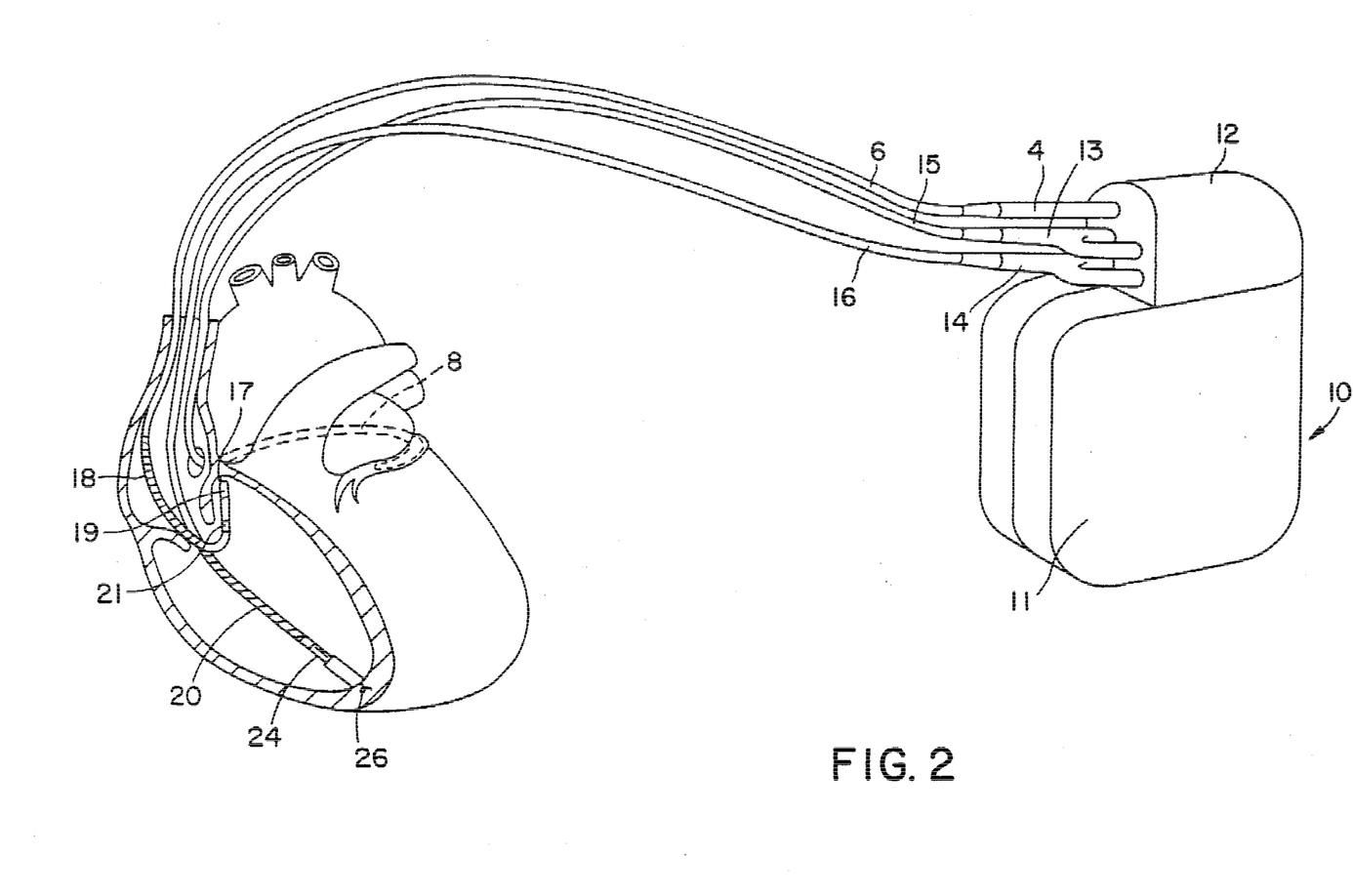
FIG. 2 illustrates the implantable PCD system of FIG. 1 in conjunction with a human heart wherein the atrial pace/sense electrodes of an atrial lead are dislodged into the right ventricle.
Figure 3:
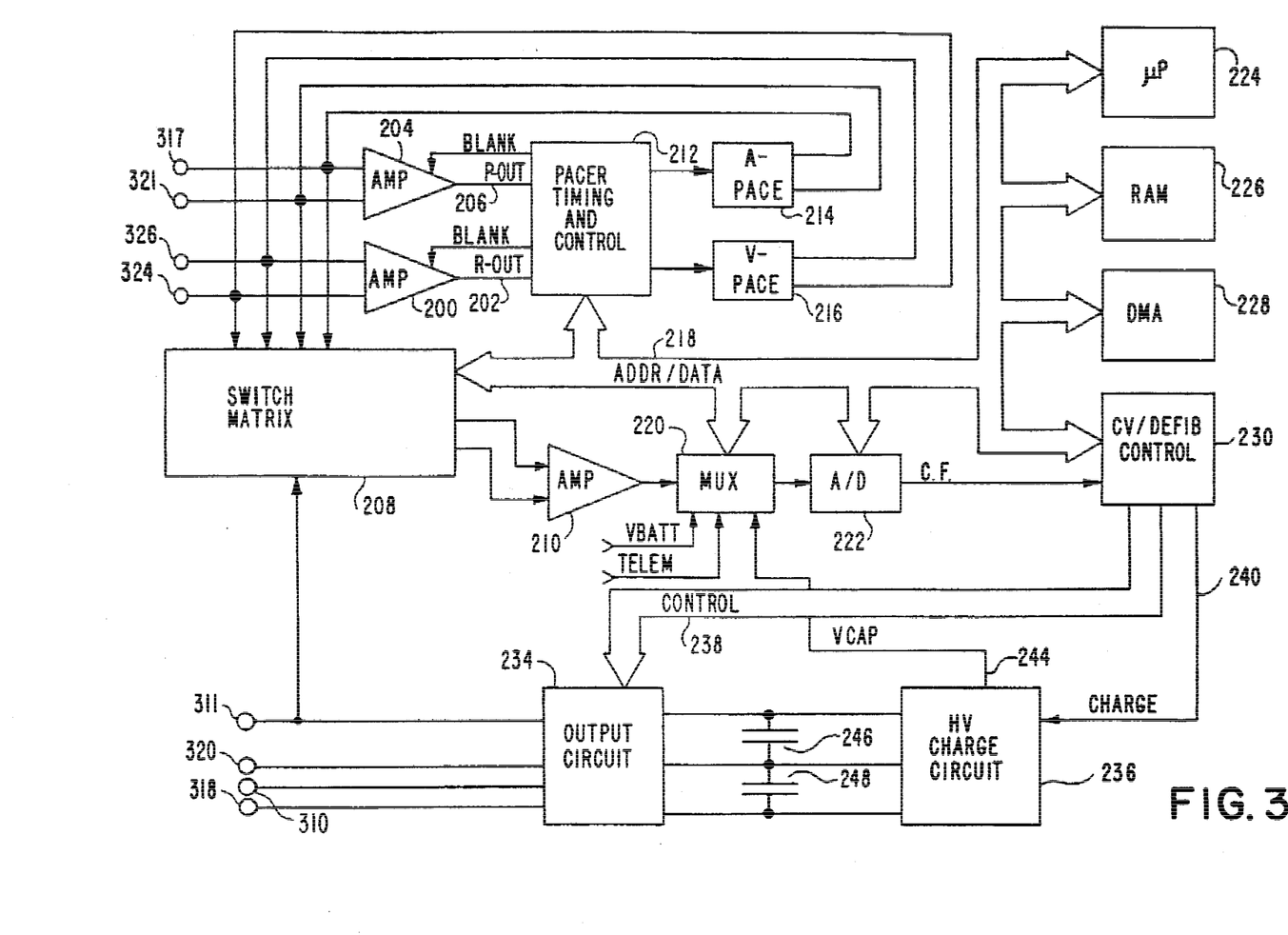
FIG. 3 illustrates a functional schematic diagram of an implantable PCD in which the invention may be practiced.
Figure 4:
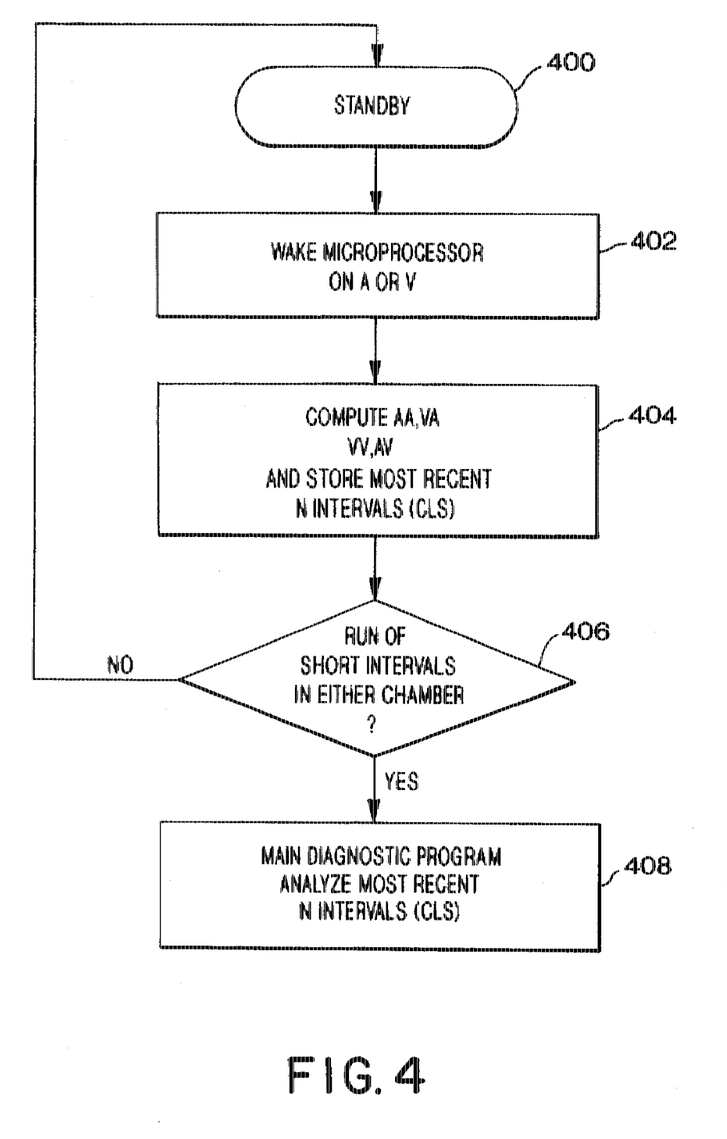
FIG. 4 is a general flow chart illustrating the steps of determining the existence of a tachyarrhythmia from A-A and V-V time intervals derived from a series of atrial and ventricular events.
Figure 5:
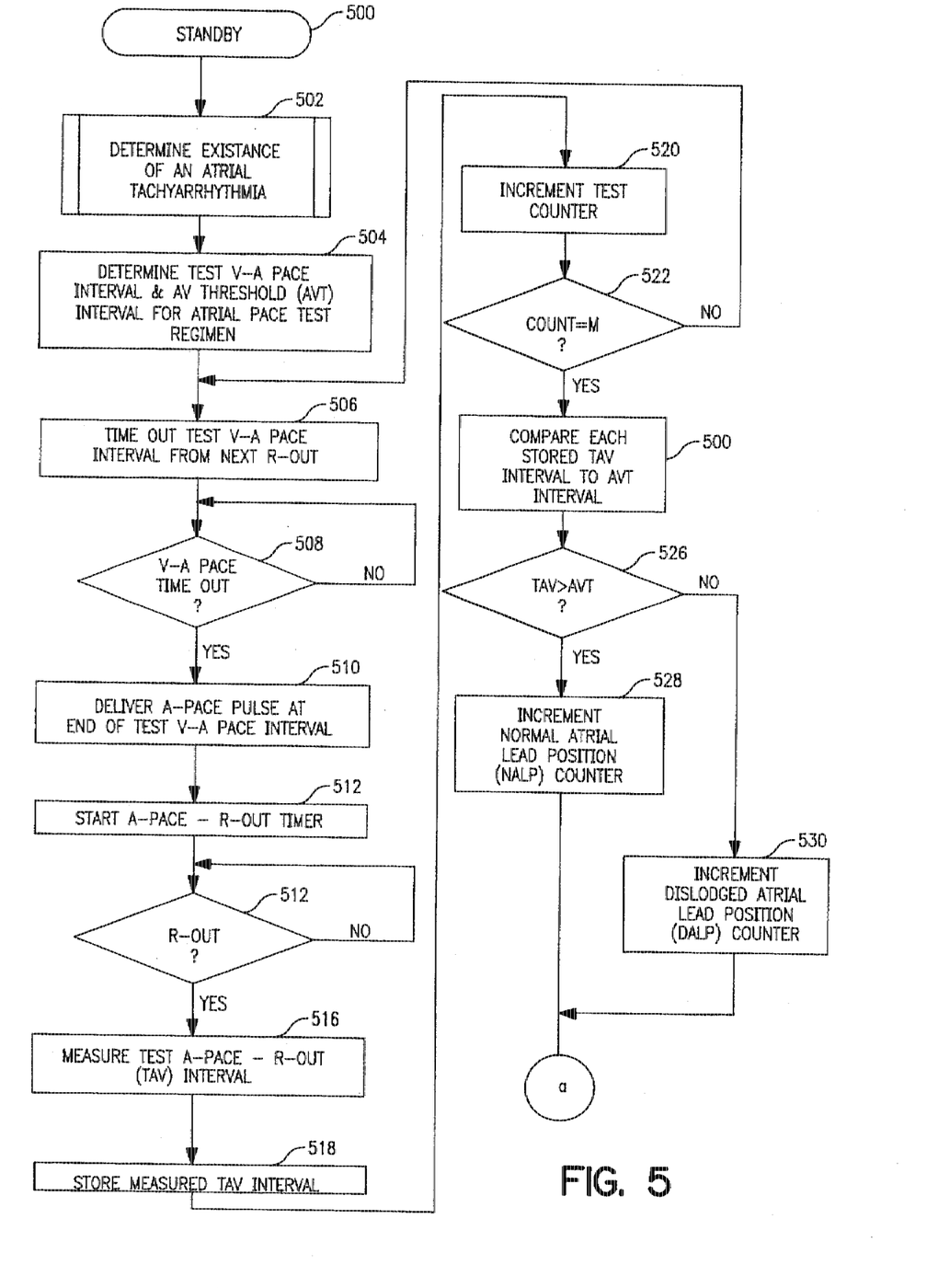
FIG. 5 is a detailed flow chart illustrating the initial steps of testing for the location of the atrial pace/sense electrode(s) starting either from an initial determination of a tachyarrhythmia following the steps of FIG. 4 or periodically.
Figure 6:
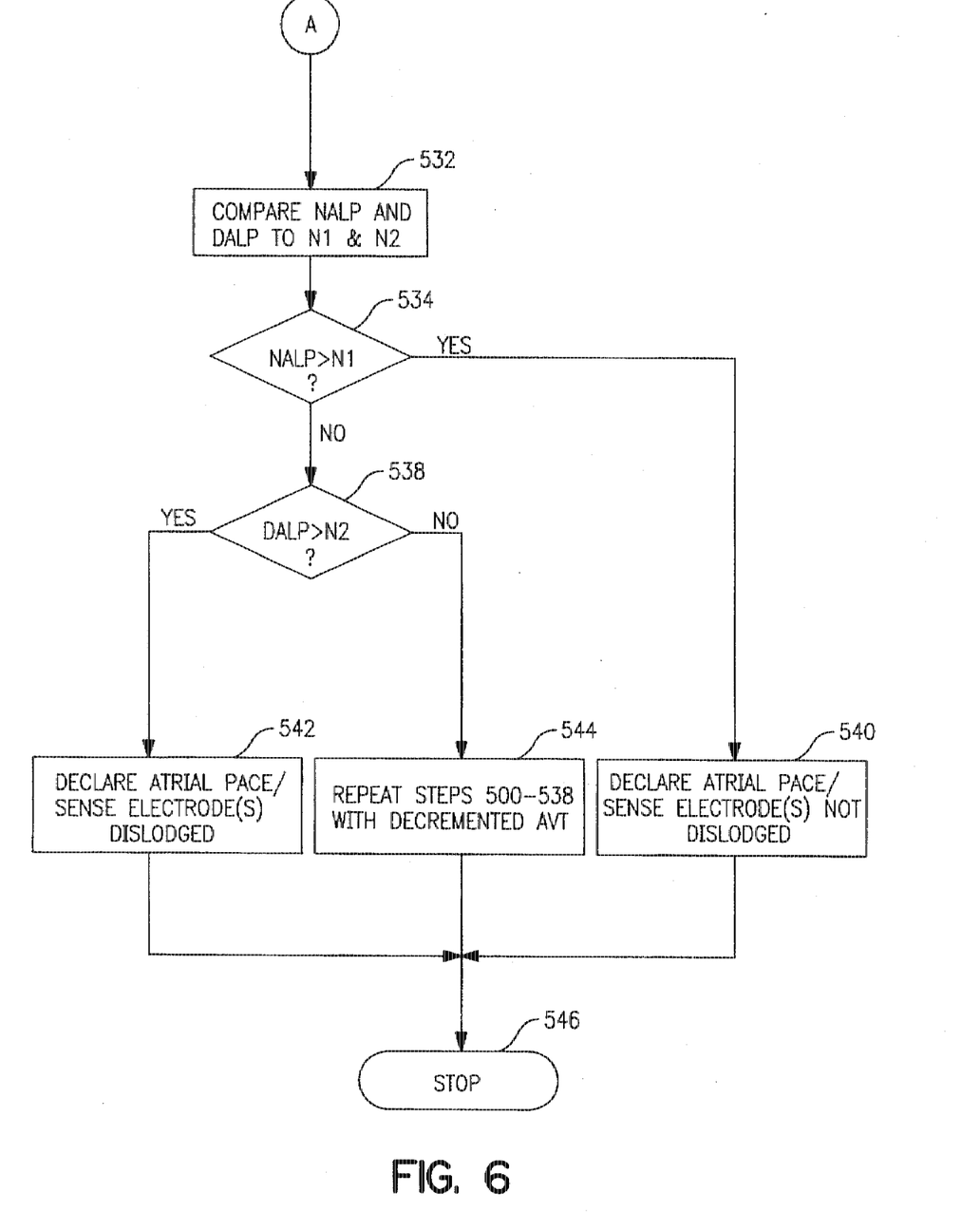
FIG. 6 is a detailed flow chart illustrating a first embodiment of the further steps for making the determination of the location of the atrial pace/sense electrodes.

FIGS. 1-3 illustrate a PCD implantable pulse generator (IPG) 10 and lead set in which the present invention may be implemented. FIG. 3 is a functional schematic diagram of the circuitry of a dual chamber, implantable PCD IPG 10 in which the present invention may usefully be practiced. Certain of the pace/sense and cardioversion/defibrillation functions and associated leads and electrodes may be disabled or not provided to configure the PCD system to operate in accordance with the preferred embodiments and variations described below. FIG. 3 should be taken as exemplary of the circuitry of the type of single chamber or dual chamber PCD IPG in which the invention may be embodied, and not as limiting, as it is believed that the invention may usefully be practiced in a wide variety of device implementations, as long as the operating mode or configuration involves use of an atrial sensing lead and atrial sense functions that may be adversely affected by dislocation of the atrial pace/sense electrode(s) from the intended site in the right atrium. In this regard, the present invention may have application in any dual chamber pacemaker without the capability of determining the existence of and responding to a tachyarrhythmia. The flow charts of FIGS. 4-6 illustrate these possible applications and embodiments of the present invention.

Turning first to the description of the leads illustrated in FIGS. 1 and 2, the right ventricular (RV) lead includes an elongated insulated lead body 16, carrying three concentric coiled wire conductors, separated from one another by tubular insulated sheaths. Located adjacent the distal end of the RV lead are a ring electrode 24, an extendible helix electrode 26, mounted retractably within an insulated electrode head 28, and an elongated, exposed coil, cardioversion/defibrillation electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors, that are fitted into a high voltage and a low voltage receptacle of the connector block assembly 12 of the PCD IPG 10. The RV cardioversion/defibrillation electrode 20 may be fabricated from platinum, platinum alloy or other materials known to be usable in implantable defibrillation electrodes and may be about 5 cm in length.

The right atrium-superior vena cava (RA/SVC) lead includes an elongated insulated lead body 15, carrying three concentric coiled conductors, separated from one another by tubular insulated sheaths, corresponding to the structure of the ventricular lead. Located adjacent the J-shaped distal end of the lead are a ring electrode 21 and an extendible helix electrode 17, mounted retractably within an insulated electrode head 19. Each of these pace/sense electrodes 17, 21 is coupled to one of the coiled conductors within the lead body 15. Pace/sense electrodes 17 and 21 are employed for atrial pacing and for sensing atrial depolarizations. An elongated RA/SVC cardioversion/defibrillation electrode 23 is optionally provided, extending proximally with respect to ring pace/sense electrode 21 and is coupled to the third conductor within the RA/SVC lead body 15. Electrode 23 preferably is 10 cm in length or greater and is intended to extend from the SVC toward the tricuspid valve in the normal fixation location depicted in FIG. 1. A bifurcated connector 13 is located at the proximal end of RA/SVC lead body 15 and carries three electrical connectors, each coupled to one of the coiled conductors, that are inserted into a high voltage receptacle and a low voltage receptacle of the connector block assembly 12 of the PCD IPG 10.

The coronary sinus (CS) lead includes an elongated insulated lead body 6, carrying one coiled conductor, coupled to an elongated, exposed coil, cardioversion/defibrillation CS electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

A PCD implantable pulse generator (IPG) 10 is shown in combination with the leads, with the lead connectors 4, 13 and 14 inserted into the receptacles of the connector block assemblies 12. Optionally, insulation of the outward facing portion of the housing 11 of the PCD IPG 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing or can 11 optionally serves as a subcutaneous defibrillation "CAN" electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two-lead system.

In FIG. 1, the atrial pace/sense electrodes 17, 21 are shown lodged into the right atrial appendage in the intended position of fixation. The distal tip, pace/sense electrode 17 in the illustrated case is formed of an active fixation helix that is screwed into the myocardium. It will be understood that the fixation mechanism may be a passive fixation mechanism as described above. At times, the fixation mechanism fails to retain the distal tip pace/sense electrode in the intended position, and, if the patient is not pacemaker dependent, the loss of atrial contact may not be noticeable to the patient. FIG. 2 illustrates the slippage of the RA/SVC lead further into the right ventricle. The distal tip and ring pace/sense electrodes may bear against the right ventricular endocardial surface and make continuous or intermittent contact. In this dislocated position, the ability to detect atrial depolarizations between the atrial pace/sense electrodes 17, 21 may be lost due to the location below the AV node of the heart and the relatively low amplitude P-wave in that location. However, the R-wave of ventricular depolarizations as well as other signals may be readily detected if there is good electrode-tissue contact or may be intermittently detected if the electrode-tissue contact is intermittent. The relatively high gain of the atrial sense amplifier in PCD IPG 10 may also contribute to mistaken sensing of other spurious signals as P-waves.

FIG. 3 is a functional schematic diagram of an implantable PCD IPG in which the present invention may usefully be practiced. This diagram should be taken as exemplary and inclusive of the major components of the type of device in which the invention may be embodied, and not as limiting, as it is believed that the invention may usefully be practiced in a wide variety of device implementations, including devices providing therapies for treating atrial tachyarrhythmias instead of or in addition to ventricular tachyarrhythmias, cardioverters and defibrillators which do not provide anti-tachycardia pacing therapies, anti-tachycardia pacers which do not provide cardioversion or defibrillation therapies, and devices which deliver different forms of anti-tachyarrhythmia therapies such as nerve stimulation or drug administration. Moreover, the invention may be practiced in a dual chamber pacemaker employing atrial and ventricular sense electrode(s) and having only bradycardia sensing, determination and pacing capabilities in one or both heart chambers.

The PCD IPG of FIG. 3 is intended to be provided with a lead system including pace/sense electrodes, which may be as illustrated in FIGS. 1 and 2, although alternative lead systems may of course be used with it, as long as an atrial lead and atrial pace/sense electrode is in the system. If the electrode configuration of FIGS. 1 and 2 is employed, the correspondence of the illustrated electrodes to the illustrated connector terminals is as follows.

Terminal 311 is adapted to be coupled with CAN electrode 11 when the CAN electrode 11 is used in the system. High voltage terminals 318, 320 and 310 are adapted to be coupled with RA/SVC cardioversion/defibrillation electrode 18, RV cardioversion/defibrillation electrode 20, and CS cardioversion/defibrillation electrode 8, respectively. Terminals 311, 318, 320 and 310 are coupled to the outputs of the high voltage output circuit 234. In alternative PCD IPG embodiments of the invention, only two or three high voltage terminals and associated electrodes may be provided. In other pacing only embodiments, the high voltage terminals and associated leads and illustrated components of FIG. 3 (described below) may be eliminated from the system.

Low voltage terminals 324 and 326 are adapted to be coupled with RV pace/sense electrodes 24 and 26, and are used for conducting ventricular sense events and pace pulses from and to the right ventricle. Low voltage terminals 317 and 321 are adapted to be coupled with RA pace/sense electrodes 17 and 21, and are used for conducting atrial sense events and pace pulses from and to the right atrium (when the atrial lead is in the normal position of FIG. 1). Terminals 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between terminals 324 and 326 exceeds the programmed sensing threshold. Terminals 317 and 321 are coupled to the P-wave amplifier 204 which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the programmed sensing threshold. The general operation of the R-wave and P-wave amplifiers 200 and 204 may correspond to that disclosed in U.S. Pat. No. 5,117,824, by Keimel, et al., incorporated herein by reference in its entirety. In any of the various embodiments of the present invention, at least the atrial and ventricular pace/sense electrode(s) and sense amplifiers 204, 200 must be present.

Switch matrix 208 is used to select which of the available terminals and associated electrodes are coupled to wide band (0.5–200 Hz) amplifier 210 for use in digital EGM signal analysis. Selection of electrodes is controlled by the microprocessor 224 via data/address bus 218, which selections may be varied as desired. Signals from the electrodes selected for coupling to bandpass amplifier 210 are provided to multiplexor 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the IPG circuitry is dedicated to the diagnosis of a bradycardia or tachyarrhythmia and the provision of cardiac pacing, cardioversion and defibrillation therapies, and, for purposes of the present invention may correspond to circuitry known in the prior art, as well as the performance of the functions and determinations of the various embodiments of the present invention illustrated in FIGS. 4–7.

The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art. Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by R-OUT and P-OUT signals on lines 202 and 206, and in accordance with the selected pacing mode, on time-out trigger generation of pacing pulses by pacer output circuits 214 and 216. The escape interval counters are also reset on generation of pacing pulses, and thereby control the basic timing of cardiac pacing functions, including anti-tachyarrhythmia pacing.

The durations of the intervals defined by the escape interval counters are determined by microprocessor 224, via data/address bus 218. The value of the count present in the escape interval counters when reset by sensed R-waves and P-waves may be used to measure the durations of V-V intervals, A-A intervals, AV intervals and V-A intervals, which measurements are stored in memory 226 and used in conjunction with the present invention to diagnose the occurrence of a variety of tachyarrhythmias and the dislocation of the atrial pace/sense electrode(s), as discussed in more detail below.

Microprocessor 224 operates as an interrupt driven device, and is responsive to interrupts from pacer timing/control circuitry 212 received via data/address bus 218 and corresponding to the occurrences of P-OUT and R-OUT signals generated by sense amplifiers 204 and 200 and corresponding to the generation of A-PACE and V-PACE cardiac pacing pulses by pacing pulse generators 214 and 216. Any necessary mathematical calculations to be performed by microprocessor 224 and any updating of the values or intervals controlled by pacer timing/control circuitry 212 take place following such interrupts. A portion of the memory 226 (FIG. 4) may be configured as a plurality of recirculating buffers, capable of holding several series of measured V-V, V-A, A-A and A-V intervals, which may be analyzed in response to the occurrence of a predetermined count of pace or sense interrupts to determine whether the patient's heart is presently exhibiting atrial or ventricular tachyarrhythmia. The intervals may be compared with various threshold intervals employed in tachyarrhythmia analysis and determination and in the practice of the present invention as described in detail below. The threshold intervals may be programmed into memory or calculated by the microprocessor and stored in memory for use in such determinations. Also counters may be configured to store counts of events and the results of comparisons during the determination of the tachyarrhythmia and the location of the atrial pace/sense electrodes The arrhythmia detection method of the present invention may include prior art tachyarrhythmia detection algorithms of the types described and referenced above in the Background of the Invention section in alternative embodiments of the invention.

The overall context for the determination of a tachyarrhythmia is set forth in FIG. 4 which is taken from the above-incorporated '910 patent. At step 400 the microprocessor 224 is in the standby mode to conserve battery power. It will be assumed that a run of high rate atrial and ventricular depolarizations are occurring such that bradycardia pacing modes are suppressed in both chambers. As in the bradycardia operating modes, when an atrial or ventricular sense event interrupt (P-OUT or R-OUT) is received from the respective sense amplifier, the microprocessor 224 awakens in step 402 to compute and store the V-A, and A-A intervals or the V-V and AV intervals, respectively. The most recent series of intervals, extending over the preceding several minutes are stored in memory on a FIFO basis, as depicted in step 404. In the event that a predetermined number of short intervals less than an atrial or ventricular tachycardia detection interval (TDI) or fibrillation detection interval (FDI) occurs during a predetermined time interval or a preceding series of heart cycles, or other criteria are satisfied, a tachycardia is provisionally determined at step 406. The main diagnostic routine for determining the type of tachycardia or other tachyarrhythmia is then entered in step S408. Preferably, the algorithms set forth in the above-referenced Gilberg et al application or the above-incorporated '910 patent are invoked at this point to provisionally identify and then confirm a specific tachyarrhythmia and invoke a therapy or series of therapies as described below.

In the event that an atrial or ventricular tachycardia is so determined, and an anti-tachycardia pacing regimen is programmed, appropriate timing intervals for controlling generation of anti-tachycardia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Circuitry may be used for controlling the timing and generation of anti-tachycardia pacing pulses as described in U.S. Pat. No. 4,577,633, issued to Berkovits et al., incorporated herein by reference.

In the event that generation of a cardioversion or defibrillation shock is programmed, microprocessor 224 employs an escape interval counter to control timing of such cardioversion and defibrillation shocks, as well as associated refractory periods. In response to the detection of atrial or ventricular fibrillation or tachyarrhythmia necessitating a cardioversion shock, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexor 220 and, in response to reaching a predetermined value set by microprocessor 224, results in generation of a logic signal on Cap Full (CF) line 254, terminating charging. Thereafter, timing of the delivery of the defibrillation or cardioversion shock is controlled by pacer timing/control circuitry 212. Following delivery of the fibrillation or tachycardia therapy, the microprocessor 224 then returns device operation to bradycardia cardiac pacing and awaits the next successive interrupt due to pacing or the occurrence of a sensed atrial or ventricular depolarization.

One embodiment of an appropriate system for delivery and synchronization of ventricular cardioversion and defibrillation shocks and for controlling the timing functions related to them is disclosed in more detail in commonly assigned U.S. Pat. No. 5,188,105 by Keimel, and incorporated herein by reference in its entirety. If atrial cardioversion/defibrillation capabilities are included in the IPG, appropriate systems for delivery and synchronization of atrial cardioversion and defibrillation therapies and for controlling the timing functions related to them may be found in PCT patent application No. WO92/18198 by Adams et al., and in U.S. Pat. No. 4,316,472 by Mirowski et al., both incorporated herein by reference in their entireties.

In addition, high frequency pacing pulse bursts may be delivered to the atrial or ventricular pace/sense electrode pairs 19, 21 or 24, 26 to terminate atrial or ventricular tachyarrhythmias, as described in PCT Patent Publication No. WO95/28987, filed by Duffin et al., and PCT Patent Publication No. WO95/28988, filed by Mehra et al., both incorporated herein by reference in their entireties.

In the illustrated PCD IPG of FIG. 3, delivery of the cardioversion or defibrillation shocks is accomplished by output circuit 234, under control of control circuitry 230 via control bus 238. Output circuit 234 determines whether a monophasic or biphasic pulse is delivered, whether the housing 11 serves as cathode or anode, and which electrodes are involved in delivery of the pulse. Examples of circuitry which may be used to control delivery of monophasic or biphasic cardioversion shocks are set forth in commonly assigned U.S. Pat. No. 5,163,427 issued to Keimel, and U.S. Pat. No. 4,953,551, issued to Mehra et al., respectively, both incorporated herein by reference.

In modern PCD IPGs, the particular therapies are programmed into memory ahead of time by the physician, and a menu of such therapies is typically provided. For example, on initial detection of an atrial or ventricular tachycardia, an anti-tachycardia pacing therapy may be selected and delivered to the chamber in which the tachycardia is diagnosed or to both chambers. On re-detection of tachycardia, a more aggressive anti-tachycardia pacing therapy may be scheduled. If repeated attempts at anti-tachycardia pacing therapies fail, a higher energy cardioversion shock may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion shocks if the rate of the detected tachycardia is above or accelerates above a preset threshold.

In the event that fibrillation is identified either initially or through progression from a tachycardia, a high frequency burst of pacing pulses may be employed as the initial attempted therapy. Subsequent therapies may be delivery of high amplitude defibrillation shocks, typically in excess of 5 joules. Lower energy levels may be employed for synchronized cardioversion shocks delivered in synchronization with an R-wave. It is envisioned that the amplitude of the defibrillation shock may be incremented in response to failure of an initial shock or shocks to terminate fibrillation.

These various types of anti-tachyarrhythmia therapies that may be employed in the PCD IPG system are merely illustrative and do not affect the present invention. However, it is recognized that the delivery of an inappropriate therapy in response to an erroneous determination of the nature of an atrial or ventricular tachyarrhythmia may have serious consequences to the patient. As described above, dislocation of the atrial pace/sense electrode(s) into the ventricle or tricuspid valve can cause such an erroneous determination due to the delivery of P-OUT signals in rapid succession in response to a variety of signal sources. The present invention is directed in this context and in other contexts to making a determination as to when an atrial lead is dislocated such that the atrial pace/sense electrode is positioned in the ventricle (e.g. the RA/SVC lead position depicted in FIG. 2), and the purported atrial sense events (the P-OUT signals of sense amplifier 204 of FIG. 3, for example) are not to be relied on or may be used to bias a determination. The electrode dislocation determination may be made in an atrial pace test sequence initiated at a given time of day or by a programmed in command during a patient work-up or upon determination of a tachyarrhythmia dependent upon the P-OUT signals. The test sequences and the determinations made from the test sequences are conducted as follows.

Figure 7:
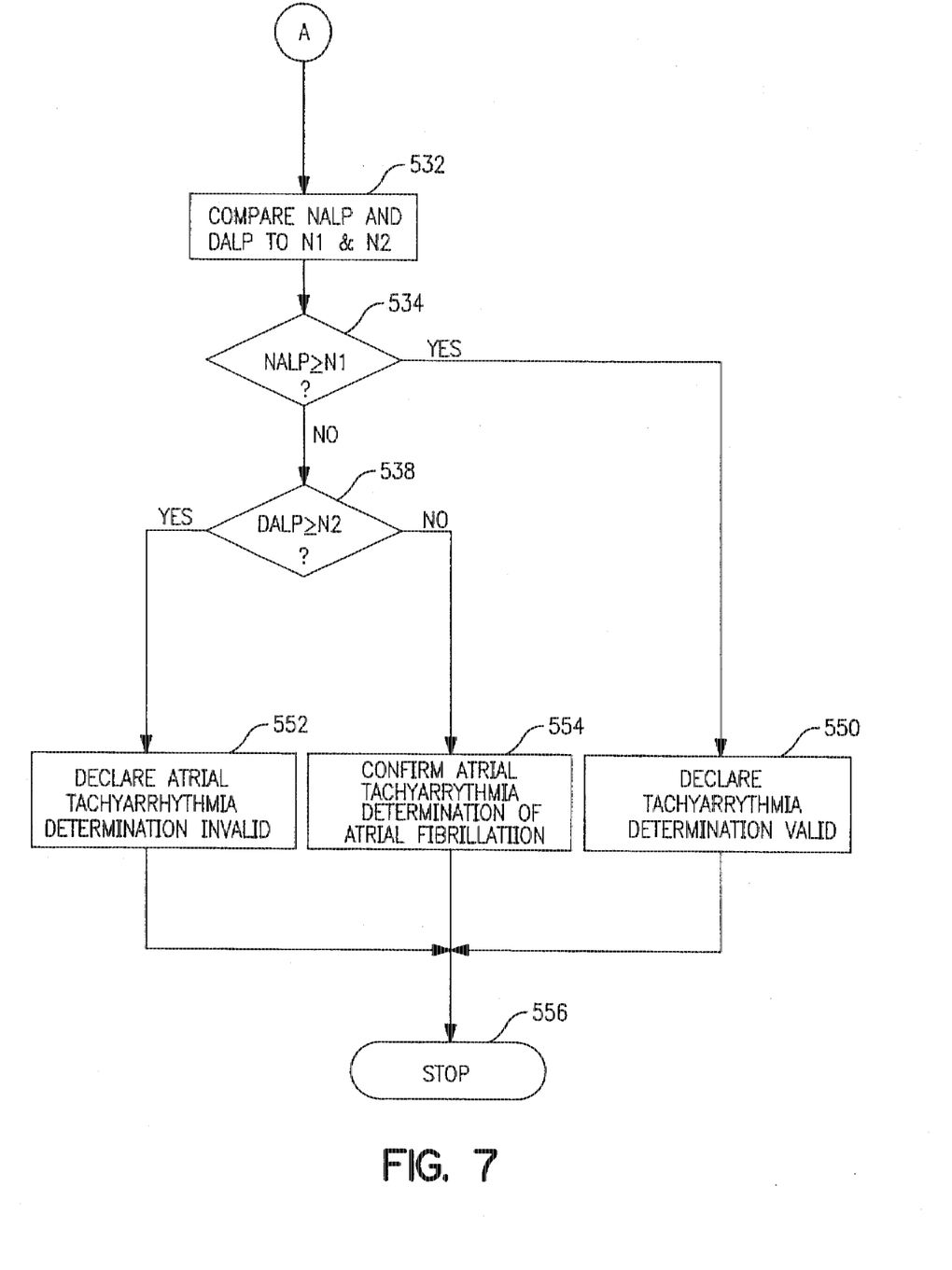
FIG. 7 is a detailed flow chart illustrating a second embodiment of the further steps for confirming or denying a determination of an atrial tachyarrhythmia made in the steps of FIG. 4.

Referring to FIG. 5, it depicts the initial steps of testing for the location of the atrial pace/sense electrode(s) starting either from an initiating event including a provisional determination of an atrial tachyarrhythmia following the steps of FIG. 4 or periodically or in response to a programmed in command. FIG. 6 illustrates a first embodiment of the further steps for making the determination of the location of the atrial pace/sense electrodes, and FIG. 7 illustrates a second embodiment of the further steps for confirming or denying a determination of an atrial tachyarrhythmia made in the steps of FIG. 4.

In FIG. 5, step 502 illustrates the provisional determination of an atrial tachyarrhythmia (which may take place in step 408 of FIG. 4) following any of the methodologies described in the prior art, e.g. those disclosed in the above-incorporated '910 patent and the above-referenced Gilberg et al application.

At this point, it should be noted that step 502 may be replaced by a substitute or additional step of simply triggering the remaining steps of the algorithm of FIG. 5 and continuing with the steps of FIG. 6 at a specific time of day or in response to a programmed in command or in response to any other trigger event or action.

Regardless of the triggering action or event, it will be presumed that the ventricular heart rate as evidenced by the prevailing stored V-V intervals (VCLs) does not evidence a ventricular tachyarrhythmia tracking or independent of the atrial tachyarrhythmia so that the ventricles can be paced at a rate exceeding the current intrinsic ventricular rate. In practice, the algorithm used in step 502 would not, in any case, provisionally determine an atrial tachyarrhythmia under such circumstances. This same condition must prevail at the time of invoking the test atrial pacing mode at a given time of day or by a programmed in command in the absence of any provisionally determined atrial tachyarrhythmia.

In step 504, the test atrial pace parameters are defined. Specifically, a V-A escape interval is defined as a percentage of the prevailing V-V escape interval and an AV threshold value is defined. A useful test V-A interval may be on the order of 80% of the prevailing V-V interval. No test V-A interval should be shorter than about 350 msec to avoid proarrhythmia that may be caused by pacing on a T-wave. Normal AV conduction times vary with the intrinsic V-V escape interval in a range of 80–150 msec, for example. When an atrial pace pulse is delivered into the ventricle at a site that is superior to the ventricular apex, e.g. the site shown in FIG. 2, and is timed at a time that evokes a ventricular depolarization, the delay until the depolarization wave is detected at the ventricular sense electrode(s) is on the order of 40–50 msec. Therefore, an AV threshold (AVT) value of 80 msec is a useful value for the normal range of ventricular rates. The sum of the test V-A interval and the AVT must be less than the prevailing intrinsic V-V interval.

The V-A test pace interval is timed out in step 506 and monitored in step 508. When it is timed out, the A-PACE test pulse is delivered in step 510 and an A-PACT—R-OUT timer is started in step 512. When the R-OUT is generated in step 514, the test A-PACT—R-OUT interval (TAV) is measured and stored in steps 516 and 518. If no R-OUT occurs within a further maximum AV delay, e.g. 150 msec (possibly longer if the patient has abnormally long AV conduction delays), then the test atrial pace pulse may be incremented in energy or the test V-A interval may be varied.

The test count of a test counter is incremented in step 520, and the test count is compared to a test count threshold, M (e.g. 8 or 16) in step 522. If the test count does not equal M, the next atrial test pulse sequence is conducted by repeating steps 506–522 upon sensing the next intrinsic R-wave generating a R-OUT.

When the test count is equal to M in step 522, the stored TAV intervals are compared to the threshold AVT interval in step 526. If the stored TAV interval is longer than the threshold AVT interval, then a normal atrial lead position (NALP) count is incremented in step 528. Similarly, if the stored TAV interval is shorter than the threshold AVT interval, then a dislodged atrial lead position (DALP) count is incremented in step 530.

If at least N of the M counts (N=6 and M=8, for example) indicate a lead dislodgement, i.e., the DALP counter is ≧ to N after M test pulses are delivered, then there is a significant probability that the atrial lead has dislodged into the ventricle. Steps 524–530 can alternatively be conducted each time that the test counter is incremented in step 522 so that a quicker determination of the trend can be made. For example, if each succeeding comparison increments the DALP count as the test pace count approaches N, then the atrial pace test mode may be prematurely terminated and other action taken. For example, the AVT may be shortened to try to find the actual A-V interval between the delivered test A-PACE and the evoked R-OUT.

At least two determinations may be made from the results of the NALP and DALP counts that may be used in different contexts. In FIG. 6, a determination is simply made that the atrial pace/sense electrode(s) is dislocated which may be of use in the context of a dual chamber bradycardia pacemaker, for example. FIG. 6 is to be interpreted in conjunction with step 502 taking any of the above-described forms. In FIG. 7, the algorithm proceeds to use the correct location or dislocation determination to confirm the presence or declare the absence of an atrial tachyarrhythmia despite the apparent rapid atrial heart rate so that an improper atrial anti-tachyarrhythmia therapy is not delivered.

In FIGS. 6 and 7, the NALP and DALP counts are compared to counter thresholds N1 and N2 at step 532 and comparison results are declared in steps 534 and 538 in each case. In FIG. 6, if NALP is determined to be greater than or equal to N1 in step 534, then the atrial pace/sense electrode (s) are declared in step 540 to be apparently not dislodged and in the proper position superior to the AV node of the heart and the current rhythm is normal sinus rhythm, based on the prevailing duration of the measured AV intervals. If DALP is greater than or equal to N2, then the atrial pace/ sense electrode(s) are declared in step 542 to be apparently dislodged and not in the proper position superior to the AV node of the heart, based on the prevailing duration of the measured AV intervals. However, if neither NALP nor DALP are greater than or equal to their respective counter thresholds, the results of the test are ambiguous and may be indicative of proper atrial lead position with the underlying rhythm being atrial fibrillation, or lead dislodgement with intermittent pacing capture. A number of possible actions may be taken in block 544, e.g. simply date stamping and storing the test results, increasing pacing output to improve capture, initiating a further test sequence with an incremented or decremented TAV interval, initiating a further diagnostic test etc. In the context of a dual chamber bradycardia pacemaker, these test results are preferably date stamped and stored in memory with or without other data that can read out by a physician and be used at a later date to diagnose the reasons why the ambiguous results were obtained at the time of the test.

In FIG. 7, steps 550–556 are substituted for steps 540–546 of FIG. 6. When NALP is greater than or equal to N1 in step 534, the atrial tachyarrhythmia determination is confirmed or declared valid in step 550 and the test atrial pace mode is stopped in step 556. If the NALP is not greater than or equal to N1 in step 534, and if DALP is greater than or equal to N2 as determined in step 538, then the provisional determination of the atrial tachyarrhythmia made in step 408 is declared invalid in step 552 and the algorithm is stopped in step 544. In this instance, there is sufficient evidence that the TAV intervals are shorter than the AVT, indicating that the atrial pace/sense electrode(s) is dislodged and that the provisional determination is unreliable. Consequently, the atrial anti-tachyarrhythmia therapies scheduled to be delivered are not delivered. If for some reason there is an error in the comparisons of the TAV intervals to the AVT threshold, and the patient is experiencing an atrial fibrillation or flutter, he/she will feel the affects of the arrhythmia and contact medical personnel to determine why no therapy was delivered. The physician may determine whether or not the atrial pace/sense electrode(s) is actually dislodged by a variety of other tests and observations made when the patient is present. In the meantime, the delivery of a potentially harmful therapy that could trigger a more serious ventricular tachyarrhythmia is avoided.

In episodes of atrial fibrillation, it is typically the case that long and short AV delay intervals shorter and longer than the AVT are spontaneously detected from the chaotic atrial electrogram. In this algorithm, if neither DALP nor NALP is greater than or equal to their respective thresholds N1 and N2, then a provisional determination of atrial fibrillation may be confirmed, or a factor may be provided that is weighed with the other factors employed in the algorithm to provisionally determine the presence of atrial fibrillation to effect the confirmation in step 554 of FIG. 7. In other words, the step of making a "provisional diagnosis" may be incomplete at step 502, that is, an atrial tachyarrhythmia may be suggested by the atrial rate without concluding even a provisional diagnosis, and the atrial pace test algorithm may be initiated so that the results may be used as a weight or factor to include in making the diagnosis. In this particular case, the factor of erratic measured AV intervals may be used to thereby "confirm" atrial fibrillation in step 554. For example, in preferred embodiments of the above-referenced Gillberg et al application, additional prerequisite criteria for delivery of anti-atrial tachyarrhythmia therapies may be included. For example, confirmation that a sinus rhythm has not resumed may also be required as a prerequisite to delivery of AF/AT therapy. An AF/AT Therapy Confirmation Criterion will prevent the initiation of atrial therapy when sinus rhythm has returned but AF/AT episode termination has not yet been detected. The AF/AT Therapy Confirmation Criterion may be satisfied for the current ventricular interval if either the number of atrial events in the current ventricular interval is greater than two, or the number of atrial events in the current ventricular interval is two and the atrial interval for both events is either less than the ATDI if AT detection is ON or AFDI if AT detection is OFF or if the confirmation of atrial fibrillation in step 554 of FIG. 7 is achieved.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

We claim:

1. A method of determining the location of the atrial pace/sense electrode(s) of an atrial pace lead in a cardiac stimulation system of the type comprising a timing and control sub-system, an atrial pulse generator coupled with the atrial pace lead for providing atrial pace pulses to the atrial pace lead, a ventricular sense amplifier coupled with a ventricular sense lead having ventricular sense electrode(s) positioned in contact with the ventricle for providing a ventricular sense signal to the timing and control sub-system, the method comprising the steps of operating the timing and control sub-system in:

(a) providing a threshold AV delay interval correlated with the AV conduction time of an atrial depolarization wave originating in the atrium and eliciting a responsive ventricular depolarization wave conducted in the ventricular septum;

(b) operating the atrial pulse generator to generate and apply an atrial pace pulse to the atrial pace electrode(s);

(c) sensing, through operation of the ventricular sense amplifier, the following ventricular depolarization at the ventricular sense electrode(s) as a ventricular sense event;

(d) measuring the time interval between the applied atrial pace pulse and the ventricular sense event as a measured AV delay interval;

(e) comparing the measured AV delay interval to the threshold AV delay interval; and (f) determining that the atrial pace electrode(s) is in contact with the right atrium if the measured AV delay interval is longer than the threshold AV delay interval.

2. The method of claim 1 wherein the determining step (f) comprises the steps of:

repeating steps (b)–(e) to derive M measured AV delay intervals and comparisons with the threshold AV delay interval; and determining that the atrial pace electrode(s) of the atrial lead are located in the right atrium when at least a number N2 of the M measured AV delay intervals are longer than the threshold AV delay interval.

3. The method of claim 2 wherein the determining step (f) further comprises the steps of:

determining that the atrial sense electrode(s) of the atrial lead are dislocated from the right atrium when a number N1 of the M measured AV delay intervals are shorter than the threshold AV delay interval.

4. The method of claim 1 further comprising the steps of:

repeating steps (b)–(e) to derive M measured AV intervals and comparisons with the threshold AV delay interval;

providing a first signal each time that the measured AV delay interval exceeds the threshold AV delay interval;

providing a second signal each time that the measured AV delay interval is less than the threshold AV delay interval; and counting the number of first and second signals provided in response to the series of M atrial pace pulses; and the determining step (f) comprises:

determining that the atrial pace electrode(s) of the atrial lead are located in the right atrium at a certain count of first signals.

5. The method of claim 4 wherein the determining step (f) further comprises the steps of:

determining that the atrial sense electrode(s) of the atrial lead are dislocated from the right atrium at a certain count of second signals.

6. The method of claim 1 wherein step (a) comprises the steps of:

measuring at least one V-V interval between successive ventricular sense events; and selecting the threshold AV delay interval as a fraction of a normal AV conduction time for the prevailing measured V-V interval(s).

7. The method of claim 1 wherein step (b) comprises the steps of:

measuring at least one V-V interval between successive ventricular sense events;

calculating a V-A escape interval as a fraction of the measured V-V interval(s);

timing the calculated V-A escape interval from a ventricular sense event; and triggering the generation of the atrial pace pulse at the time-out of the calculated V-A escape interval.

8. Apparatus for determining the location of the atrial pace electrode(s) of an atrial pacing lead in a cardiac stimulation system of the type comprising a timing and control sub-system, an atrial pulse generator coupled with the atrial pace lead for providing atrial pace pulses to the atrial pace lead, and a ventricular sense amplifier coupled with a ventricular sense lead having ventricular sense electrode(s) positioned in contact with the ventricle for providing a ventricular sense signal to the timing and control sub-system, the apparatus further comprising:

(a) means for providing a threshold AV delay interval correlated with the AV conduction time of an atrial depolarization wave originating in the atrium and eliciting a responsive ventricular depolarization wave conducted in the ventricular septum;

(b) means for operating the atrial pulse generator to generate and apply an atrial pace pulse to the atrial pace electrode(s);

(c) means for sensing, through operation of the ventricular sense amplifier, the following ventricular depolarization at the ventricular sense electrode(s) as a ventricular sense event;

(d) means for measuring the time interval between the applied atrial pace pulse and the ventricular sense event as a measured AV delay interval;

(e) means for comparing the measured AV delay interval to the threshold AV delay interval; and (f) means for determining that the atrial pace electrode(s) is in contact with the right atrium if the measured AV delay interval is longer than the threshold AV delay interval.

9. The apparatus of claim 8 wherein the determining means further comprises:

means for operating means (b)–(e) to derive M measured AV delay intervals and comparisons with the threshold AV delay interval; and means for determining that the atrial pace electrode(s) of the atrial lead are located in the right atrium when a certain count N2 of the M measured AV delay intervals are consistently longer than the threshold AV delay interval.

10. The apparatus of claim 9 wherein the determining means (f) comprises:

means for determining that the atrial sense electrode(s) of the atrial lead are dislocated from the right atrium when a certain count N1 of the M measured AV delay intervals are shorter than the threshold AV delay interval.

11. The apparatus of claim 9 wherein the determining means (f) comprises:

means for operating means (b)-(e) to derive M measured AV intervals and comparisons with the threshold AV delay interval;

means for providing a first signal each time that the measured AV delay interval exceeds the threshold AV delay interval;

means for providing a second signal each time that the measured AV delay interval is less than the threshold AV delay interval;

means for counting the number of first and second signals provided in response to the series of M atrial pace pulses; and means for determining that the atrial pace electrode(s) of the atrial lead are located in the right atrium at a certain count of first signals.

12. The apparatus of claim 11 wherein the determining means (f) further comprises:

means for determining that the atrial sense electrode(s) of the atrial lead are dislocated from the right atrium at a certain count of second.

13. The apparatus of claim 8 further wherein the threshold AV delay interval providing means (a) further comprises:

means for measuring the V-V interval between successive ventricular sense events; and means for selecting the threshold AV delay interval as a fraction of a normal AV conduction time for the prevailing sensed V-V interval.

14. The apparatus of claim 8 wherein:

the means (b) for operating the atrial pulse generator further comprises:

means for measuring at least one V-V interval between successive ventricular sense events; and means for calculating a V-A escape interval as a fraction of the measured V-V interval(s); and the means for operating the atrial pulse generator further comprises:

means for timing the calculated V-A escape interval from a ventricular sense event; and means for triggering the generation of the atrial pace pulse at the time-out of the calculated V-A escape interval.

15. A method of confirming a provisional diagnosis of an atrial tachyarrhythmia in a dual chamber, anti-tachyarrhythmia cardiac stimulation system of the type comprising a timing and control sub-system, an atrial sense amplifier and atrial pulse generator coupled with an atrial pace/sense lead, the atrial sense amplifier providing atrial sense signals to the timing and control sub-system and the atrial pulse generator providing atrial pace pulses to the atrial pace/sense lead, a ventricular sense amplifier coupled with a ventricular sense lead having ventricular sense electrode(s) positioned in contact with the ventricle for providing a ventricular sense signal to the timing and control sub-system, the method comprising the steps of operating the timing and control sub-system in:

(a) provisionally diagnosing the existence of an atrial tachyarrhythmia from the atrial sense signals;

(b) providing a threshold AV delay interval correlated with the AV conduction time of an atrial depolarization wave originating in the atrium and eliciting a responsive ventricular depolarization wave conducted in the ventricular septum;

(c) operating the atrial pulse generator to generate and apply an atrial pace pulse to the atrial pace/sense electrode(s);

(d) sensing, through operation of the ventricular sense amplifier, the following ventricular depolarization at the ventricular sense electrode(s) as a ventricular sense event;

(e) measuring the time interval between the applied atrial pace pulse and the ventricular sense event as a measured AV delay interval;

(f) comparing the measured AV delay interval to the threshold AV delay interval;

(g) confirming the provisional diagnosis when the measured AV delay interval is longer than the threshold AV delay interval signifying that the atrial pace/sense electrode(s) are located within the right atrium.

16. The method of claim 15 further comprising the steps of:

repeating steps (c)-(f) to derive M measured AV delay intervals and comparisons with the threshold AV delay interval; and wherein the confirming step (g) further comprises:

confirming the provisional diagnosis of atrial tachyarrhythmias when a certain count N1 of the M measured AV delay intervals are consistently longer than the threshold AV delay interval indicating that the atrial pace/sense electrode(s) of the atrial lead are located in the right atrium.

17. The method of claim 16 further comprising the step of:

(h) canceling the provisional diagnosis of an atrial tachyarrhythmia when a certain count N2 of the M measured AV delay intervals are consistently shorter than the threshold AV delay interval indicating that the atrial pace/sense electrode(s) of the atrial lead are dislocated from the right atrium.

18. The method of claim 15 further comprising the steps of:

repeating steps (c)-(f) to derive M measured AV intervals and comparisons with the threshold AV delay interval;

providing a first signal each time that the measured AV delay interval exceeds the threshold AV delay interval;

providing a second signal each time that the measured AV delay interval is less than the threshold AV delay interval; and counting the number of first and second signals provided in response to the series of M atrial pace pulses; and wherein the confirming step (g) comprises:

confirming the provisional diagnosis of an atrial tachyarrhythmia at a certain count of first signals.

19. The method of claim 18 wherein the confirming step (g) further comprises the steps of:

denying the confirmation of the atrial tachyarrhythmia at a certain count of second signals.

20. The method of claim 15 further comprising the steps of:

repeating steps (c)–(f) to derive M measured AV intervals and comparisons with the threshold AV delay interval;

providing a first signal each time that the measured AV delay interval exceeds the threshold AV delay interval;

providing a second signal each time that the measured AV delay interval is less than the threshold AV delay interval; and counting the number of first and second signals provided in response to the series of M atrial pace pulses; and the confirming step (g) further comprises:

confirming a provisional diagnosis of atrial tachyarrhythmia when the numbers of first and second signals are both greater than zero.

21. The method of claim 15 wherein step (b) comprises the steps of:

measuring at least one V-V interval between successive ventricular sense events; and selecting the threshold AV delay interval as a fraction of a normal AV conduction time for the prevailing measured V-V interval(s).

22. The method of claim 15 further wherein step (c) comprises the steps of:

measuring at least one V-V interval between successive ventricular sense events;

calculating a V-A escape interval as a fraction of the measured V-V interval(s);

timing the calculated V-A escape interval from a ventricular sense event; and triggering the generation of the atrial pace pulse at the time-out of the calculated V-A escape interval.

23. Apparatus for confirming a provisional diagnosis of an atrial tachyarrhythmia in a dual chamber, anti-tachyarrhythmia cardiac stimulation system of the type comprising a timing and control sub-system, an atrial sense amplifier and atrial pulse generator coupled with an atrial pace/sense lead, the atrial sense amplifier providing atrial sense signals to the timing and control sub-system and the atrial pulse generator providing atrial pace pulses to the atrial pace/sense lead, a ventricular sense amplifier coupled with a ventricular sense lead having ventricular sense electrode(s) positioned in contact with the ventricle for providing a ventricular sense signal to the timing and control sub-system, the apparatus further comprising:

(a) means for provisionally diagnosing the existence of an atrial tachyarrhythmia from the atrial sense signals;

(b) means for providing a threshold AV delay interval correlated with the AV conduction time of an atrial depolarization wave originating in the atrium and eliciting a responsive ventricular depolarization wave conducted in the ventricular septum;

(c) means for operating the atrial pulse generator to generate and apply an atrial pace pulse to the atrial pace/sense electrode(s);

(d) means for sensing, through operation of the ventricular sense amplifier, the following ventricular depolarization at the ventricular sense electrode(s) as a ventricular sense event;

(e) means for measuring the time interval between the applied atrial pace pulse and the ventricular sense event as a measured AV delay interval;

(f) means for comparing the measured AV delay interval to the threshold AV delay interval;

(g) means for confirming the provisional diagnosis of atrial tachyarrhythmia if the measured AV delay interval is longer than the threshold AV delay interval.

24. The apparatus of claim 23 further comprising:

means for employing means (c)–(f) to derive M measured AV delay intervals and comparisons with the threshold AV delay interval; and wherein the confirming means (g) comprises:

means for confirming the provisional diagnosis of atrial tachyarrhythmias when at least N1 of the M measured AV delay intervals are longer than the threshold AV delay interval.

25. The apparatus of claim 24 wherein said confirming means (g) further comprises:

means for canceling the provisional diagnosis of atrial tachyarrhythmia when at least N2 of the M measured AV delay intervals are shorter than the threshold AV delay interval.

26. The apparatus of claim 23 further comprising:

means for operating means (c)–(f) to derive M measured AV intervals and comparisons with the threshold AV delay interval;

means for providing a first signal each time that the measured AV delay interval exceeds the threshold AV delay interval;

means for providing a second signal each time that the measured AV delay interval is less than the threshold AV delay interval; and means for counting the number of first and second signals provided in response to the series of N atrial pace pulses; and wherein the confirming means (g) comprises:

means for confirming the provisional diagnosis of an atrial tachyarrhythmia at a certain count of first signals.

27. The apparatus of claim 26 wherein the confirming means (g) further comprises:

means for denying the confirmation of the atrial tachyarrhythmia at a certain count of second signals.

28. The apparatus of claim 23 further comprising:

means for operating means (c)–(f) to derive M measured AV intervals and comparisons with the threshold AV delay interval;

means for providing a first signal each time that the measured AV delay interval exceeds the threshold AV delay interval;

means for providing a second signal each time that the measured AV delay interval is less than the threshold AV delay interval; and means for counting the number of first and second signals provided in response to the series of atrial pace pulses; and the confirming means (g) further comprises:

means for confirming a provisional diagnosis of atrial fibrillation when the numbers of first and second signals are both greater than zero.

29. The apparatus of claim 23 wherein the means (b) for providing a threshold AV delay interval further comprises:

means for measuring at least one V-V interval between successive ventricular sense events; and means for selecting the threshold AV delay interval as a fraction of a normal AV conduction time for the prevailing measured V-V interval(s).

30. The apparatus of claim 23 further wherein the means (c) for operating the atrial pulse generator comprises:

means for measuring at least one V-V interval between successive ventricular sense events;

means for calculating a V-A escape interval as a fraction of the measured V-V interval(s);

means for timing the calculated V-A escape interval from a ventricular sense event; and means for triggering the generation of the atrial pace pulse at the time-out of the calculated V-A escape interval.

* * * * *